United States Patent [19]

Frankel

[11] Patent Number: 4,582,787

[45] Date of Patent: Apr. 15, 1986

[54] METHOD OF TESTING A PATIENT FOR A PREDISPOSITION TO LUNG CANCER, CERTAIN OTHER CANCERS, NEUROFIBROMATOSIS AND CERTAIN OTHER HEREDITARY DISORDERS

[76] Inventor: Jack W. Frankel, 730 126th Ave., Treasure Island, Fla. 33706

[21] Appl. No.: 454,880

[22] Filed: Dec. 30, 1982

[51] Int. Cl.$^4$ .............................................. C12Q 1/70
[52] U.S. Cl. ......................................................... 435/5
[58] Field of Search ............................................. 435/5

[56] References Cited

U.S. PATENT DOCUMENTS 3,575,812  4/1971  Chappelle .............................. 435/5
3,673,410  6/1972  Waite et al. ............................ 435/5

OTHER PUBLICATIONS

Kaplan et al., Chem. Abst., vol. 98 (1983), p. 957r.
Gottesman—Chem. Abst., vol. 89 (1978), pp. 105, 445q.
Klement et al—J. Nat. Canc. Inst., vol. 47, No. 1, Jul. 1971, pp. 65–73.
Kopelovich—Cancer, vol. 40, No. 5 (1977), pp. 2534–2541.
Pfeffer et al.-Cell-vol. 10 (1977), pp. 313–320.
J. W. Frankel, P. Bidot, H. V. Samis, Feasability Study of a Diagnostic Test to Identify Individuals at Risk for Cancer, 9-4-81, Proceedings of the Xth International Symposium for Comparative Research on Leukemia and Related Diseases, pp. 555–556.
J. W. Frankel, P. Bidot, H. V. Samis, Feasability Study of a Diagnostic Test to Identify Individuals at Risk for Cancer, Abstracts of the Xth International Symposium for Comparative Research on Leukemia and Related Diseases, University of CA, 9-4-81, p. 158.
P. Bidot, J. W. Frankel, Enhanced Viral Transformation in Skin Fibroblasts from Neurofibromatous Patients, 1983, pp. 27–32, vol. 13 of the Annuals of Clinical and Laboratory Science.
J. W. Frankel, P. Bidot, H. Samis and V. Bergs, Enhanced Viral Transformation of Skin Fibroblast Cultures from Patients Afflicted with Neurofibromatosis, May 25-28, 1983, vol. 24, p. 123, The Proceedings of the American Association of Cancer Research.
J. W. Frankel, P. Bidot, H. Samis, V. Bergs, Enhanced Viral Transformation of Skin Fibroblasts from Patients Affected with Neurofibromatosis, 10-2-82, p. 26, Proceedings of the Annual Meeting of Southeastern and South Carolina Branches of the American Society for Microbiology.

*Primary Examiner*—Sam Rosen
*Attorney, Agent, or Firm*—Frijouf, Rust & Pyle

[57] ABSTRACT

A method is disclosed for testing a patient to determine a predisposition to lung cancer and neurofibromatosis. The method comprises the steps of carrying out a biopsy on each patient of a first group of patients known to have a cancer or a cancer with a known hereditary component such as neurofibromatosis, the biopsy including the removal of a skin sample from each patient. The removed skin samples are prepared for in vitro testing thereof, initially to prove contamination is not present. In vitro testing is carried out to determine whether viral transformation of cultures established from the skin samples exists. Portions of Kirsten murine sarcoma virus are prepared and added to the uncontaminated cultured skin cells. The skin cells treated with the Kirsten murine sarcoma virus are incubated and a viral assay is performed to determine which skin cultures have been transformed due to the treatment with Kirsten murine sarcoma virus. The foregoing steps are performed relative to a second group of cancer and neurofibromatosis-free patients. An index is composed from the results of the assays performed on the first and second groups of patients. The foregoing steps are repeated relative to a subsequent patient, the predisposition to lung cancer and/or neurofibromatosis of which is unknown and a comparison of the results obtained from the assay relative to the subsequent patient is compared with the index to determine whether a predisposition to lung cancer and neurofibromatosis exists relative to the subsequent patient.

32 Claims, 1 Drawing Figure

METHOD OF TESTING A PATIENT FOR A PREDISPOSITION TO LUNG CANCER, CERTAIN OTHER CANCERS, NEUROFIBROMATOSIS AND CERTAIN OTHER HEREDITARY DISORDERS

BACKGROUND OF THE INVENTION

1. Field of the Invention

This invention relates to a method of testing a patient to determine a predisposition to certain cancers and certain diseases with a hereditary background.

2. Description of the Prior Art

The American Cancer Society estimates that in the United States alone, approximately one person dies from cancer every eighty seconds. It has also ben estimated that 117,000 deaths from cancer that occurred in 1978 could have been prevented by earlier diagnosis and treatment. The primary goal of public health is to prevent diseases rather than the treatment of disease.

It is well known among cancer research workers that certain factors are closely related to the instance of cancer. Among these factors are to be mentioned the history of cancer within the family, environment and personal habits such as smoking. If a predisposition of a person to cancer were known, the predisposition would permit the early diagnosis of the existence of cancer. Such a predisposition would als facilitate the possibility of early remedial treatment thereof.

Various diagnostic techniques have been employed in the past in an effort to diagnose the existence at an early stage of the development of cancer within a patient. Such prior art techniques suffered from several inherent problems. Firstly, such techniques have often proved unreliable in diagnosing the existence of cancer. Secondly, such prior art diagnostic tools have merely established the existence of cancer within the patient, but have not been able to determine the predisposition of a patient to the occurrence of a cancerous disorder. Thirdly, the cost of conducting such prior art methods of diagnosis has usually proved to be prohibitive.

In order to achieve the important goal of preventing lung cancer, certain cancers and other hereditary diseases, the object of the present invention is to identify those individuals at relatively high risk for developing this malignancy or other disease prior to detection of frank or metastatic growth. This invention is based on observations made during in vitro studies of cellular transformation, particularly of skin fibroblast cells derived from patients who are genetically susceptible to cancer. These findings revealed increased oncogenic virus transformation of cultured fibroblasts derived from such patients.

The present invention is specifically aimed at assessing a convenient, reliable, and rapid in vitro virus transformation assay as a diagnostic index to identify those persons susceptible to certain diseases such as smokers who are at increased risk for subsequent development of lung cancer.

The present invention is founded on laboratory, clinical and epidemiological observations of cancer which clearly suggest genetic as well as environmental predisposing factors in the etiology of disease. It is important to develop a diagnostic procedure that can identify smokers and non-smokers in the population who may be at increased genetic risk for developing lung cancer and possibly other neoplastic diseases. The need for such a procedure is paramount, since present diagnostic procedures and treatment of lung and other cancers, even when applied rigorously, result only in a modest enhancement of survival rate as described in Brett, G. Z.; "Earlier Diagnosis and Survival in Lung Cancer", British Medicine. 4:260-262, 1969.

In the identification of genetic conditions that predispose to cancer, a number of widely diverse studies have been conducted in attempts to identify susceptible individuals. An example of one of these approaches concerned experiments conducted to detect the sensitivity of cells with gross chromosomal aberrations followed by increased spontaneous chromosomal breakage to certain carcinogens. In these instances, the premise was to ultimately detect cytogenetically normal cells that possessed enhanced susceptibility to cancer. In measuring chromosomal breaks per radiation dose, fibroblasts and lymphocytes from Fanconi's anemia exhibited a significantly greater sensitivity to X-ray (Higuraski, M., Conen P. E.: "In Vitro Chromosomal Radiosensitivity in Fanconi's Anemia", Blood. 38:336-342, 1971). Fanconi's anemia is an autosomal recessive disease which is associated with a high incidence of chromosome aberrations and a greatly increased risk of neoplasia (Bloom G. E. Warner S., Gerald P. S., Diamond L. K.: "Chromosome Abnormalities in Constitutional Aplastic Anemia", New England Journal of Medicine. 274:8-14, 1966 and Swift M. R., Hirschhorn K.: "Fanconi's Anemia: Inherited Susceptibility to Chromosome Breakage in Various Tissues", Annals Internal Medicine. 65:496-503, 1966).

Further, cells from patients with Fanconi's anemia or Down's Syndrome (trisomy 21) showed an increased percentage of endoreduplication and tetrapoloidy in studies with the chemical carcinogen, benzpyrene (Hirschhorn K., Block-Shtacher N.: "Transformation of Genetically Abnormal Cells", In The University of Texas M.D. Anderson Hospital and Tumor Institute at Houston, 23rd Annual Symposium on Fundamental Cancer Research, 1969: Genetic Concepts and Neoplasia. Baltimore, Williams & Wilkins, 1970 pp. 191-202). Down's Syndrome is another disease associated with an abnormally high incidence of tumors (Krivit W., Good R. A.: "Simultaneous Occurrence of Mongolism and Leukemia", American Journal of Diseases of Children. 94:289-293, 1957 and Holland W. W., Doll R., Carter C. O.: "The Mortality From Leukemia and Other Cancers Among Patients with Down's Syndrome (Mongols) and Among Their Parents", British Journal of Cancer 16:177-186, 1962); the nature of the chromosome abnormality of Down's Syndrome is, however, fundamentally quite different from that of Fanconi's anemia.

The present invention seeks to identify smokers at high risk for developing lung cancer is based upon previous studies that have utilized quantitative in vitro virus transformation of human cells. The method can provide a convenient, reliable and rapid test for assessing predisposition to lung cancer in individuals in the population with particular emphasis on those who are heavy smokers. This information is critical to any Public Health program and is designed to prevent or circumvent this disease.

Genetic factors have been shown to play a dominant role in Rous sarcoma virus focus formation in chick cells and tumor formation in the chick (Payne L. N., Briggs P. M.: "Differences Between Highly Inbred Lines of Chickens in the Response to Rous Sarcoma Virus of the Chorioallantoic Membrane and of Embryonic Cells in Tissue Culture", Virology. 24:610-616, 1964 and Vogt P. K., Ishizaki R: "Reciprocal Patterns of Genetic Resistance to Avian Tumor Viruses in Two Lines of Chickens", *Virology.* 26:665-667, 1965). Other studies described the influence of the cell genotype on transformation of human skin fibroblasts by oncogenic viruses. These studies were guided by early evidence that persons at high risk for cancer could be identified by relative susceptibility rate to oncogenic sarcoma virus transformation of their cultured skin fibroblasts (Higuraski M., Todaro G. J.: "Viral Transformation of Cells from Persons at High Risk of Cancer ", *Lancet.* 1:81-82, 1969).

Inoculation of fibroblast cultures from patients with Fanconi's anemia with simian virus 40 (SV40) and an adenovirus 7-SV40 "hybrid" revealed a much greater susceptibility of these cells to transformation when compared with fibroblast strains developed from normal individuals and from individuals not associated with increased tumor incidence (Todaro G. J., Green H, Swife M. R.: "Susceptibility of Human Diploid Fibroblast Strains to Transformation by SV40 Virus", *Science.* 153:1252-1254, 1966). Multiple tumor biopsies from the same person led to cell strains that were very similar in their transformation susceptibility with SV40 (Todaro G. J., Aaronson S. A.: "Human Cell Strains Susceptible to Focus Formation by Human Adenovirus Type 12", *Proceedings of the National Academy of Science, U.S.A.* 61:1272-1278, 1968). Subsequent results showed that skin fibroblast cultures from patients with Down's Syndrome are intrinsically more susceptible to in vitro transformation by SV40 than are normal cell cultures (Todaro G. J., Martin G. M.: "Increased Susceptibility of Down's Syndrome Fibroblasts to Transformation by SV40", *Proceedings of the Society of Experimental Biology and Medicine.* 124:1232-1236, 1967). The human fibroblasts that were highly susceptible to transformation by SV40 were subsequently tested with human adenovirus type 12, and these cultures developed foci of altered cells with much greater frequency than did the normal human cell cultures (Todaro, Aaronson, "Human Cell Strains, etc." pp. 1272-1278). Moloney murine sarcoma virus is an RNA-containing tumor virus (Huebner R. J.: "The Murine Leukemia-Sarcoma Virus Complex", *Proceedings of the National Academy of Science, U.S.A.* 58:835-842, 1967) has also been demonstrated to cause transformation of human fibroblast strains derived from a variety of sources, including adult skin (Aaronson S. A., Todaro G. J.: "Transformation and Virus Growth by Murine Sarcoma Viruses in Human Cells", *Nature.* 225:458-459, 1970).

The Kirsten strain of murine sarcoma virus (KiMSV) from a KiMSV transformed rat cell line (Klement V., Hartley J. W., Rowe W. P., Huebner R. J.: "Recovery of a Hamster-Specific, Focus-Forming, and Sarcomagenic Virus From a 'Non-Infectious' Hamster Tumor Induced by the Kirsten Mouse Sarcoma Virus", *Journal of the National Cancer Institute* 43:925-933, 1968), also induced morphological transformation in cultured human cells (Aaronson, S. A., Todaro G. J.: "Transformation and Virus Growth etc." pp.458-459). KiMSV is a sarcomagenic isolate from a rate-passaged murine erythroblastosis virus that shares the rat sarcoma genome with other rat sarcomas (Rhim J., Vernon J., Dug F., Huebner R. J.: "Wide Host Range of Murine Sarcoma Virus", *International Journal of Cancer* 12:734-741, 1973). The morphological alternations of the KiMSV tranformed foci are characterized by refractile spindle-shaped and round cells which grow on top of the monolayers and exhibit large cytoplasmic vacuoles.

This invention utilizes KiMSV in the transformation studies since it has been shown that KiMSV is more efficient than MMSV in transforming human cell cultures (Aaronson S. A., Todaro G. J.: "Transformation and Virus Growth, etc." pp. 458-459). This may well due to the KiMSV-associated xenotropic helper virus rather than to the sarcoma genome itself (Aaronson S., Weaver C.: "Characterization of Murine Sarcoma Virus (Kirsten) Transformation of Mouse and Human Cells", *Journal of General Virology.* 13-245-252, 1971). The change in morphology is focal and can be quantitatively evaluated by absolute virus dose required to effect transformation (Klement V., Freedman M. H., McAllister R. M., Nelson-Rees W. A., Huebner R. J.: "Differences in Susceptibility of Human Cells to Mouse Sarcoma Virus", *Journal of the National Cancer Institute.* 47-65-73, 1971). The susceptibility of 18 individual fibroblast strains to transformation varied more than 300-fold (ibid). In general, as were the findings cited above relative to SV40, adenovirus and MMSV, more susceptibile cell strains were found among those derived from individuals with neoplasia and genetic or chromosomal abnormalities than those derived from "normal" individuals and fetuses (ibid). In the present invention, it was noted that: (1) Tissue cultures derived from various organs from human fetuses revealed the same type of sensitivity; (2) The cultures with low sensitivity to transformation were transformed with higher titers of KiMSV than were required for susceptible cells; and (3) A high sensitivity of some apparently "normal" human cells was observed. The findings that cell strains from apparently "normal" individuals or fetuses showed high sensitivity to focus formation is of special interest. Such individuals may well represent a specific group of "high risk persons" with an enhanced predisposition to cancer.

Hereditary adenomatosis of the colon and rectum (AGR) is a disorder in which numerous polyps develop in the gastrointestinal tract (Frameni J. Jr.: "Genetic Factors", In J. Holland and E. Frei (eds.) *Cancer Medicine.* pp. 7-15, Philadelphia, Lea and Febinger, 1973 and Knudson A. Jr., Strong L., Anderson D.: "Heredity and Cancer in Man", In A. Steinberg and A. Bearn (eds.), *Progress in Medical Genetics,* 9 pp. 113-158, New York, Grune and Stratton, 1973). Within the familial proband, it is clearly established that 50 percent of the members are at 90-100 percent risk of colon cancer (Dr. R. J. Huebner, personal communication). This trait is carried by an autosomal dominant gene, although it seems probable that additional genes may pleiotropically modify its expression (Alm T., Licznerski G.: "The Intestinal Polyposes", In R. McConnel (ed.) *Clinics in Gastroenterology,* pp. 577-601, Philadelphia, Saunders, 1973; and Gardner E., Richards R.: "Multiple Cutaneous and Subcutaneous Lesions Occurring Simultaneously with Hereditary Polyposis and Osteomatosis", *American Journal of Human Genetics.* 5:139-149, 1953; And McConnel R. B.: *The Genetics of Gastrointestinal Disorders.* London, Oxford University Press, 1966, pp. 1-282; and Morson B., Bussey H.: "Predisposing Causes of Intestinal Cancer", in *Current Problems in Surgery.* Chicago, Yearbook Medical Publishers, 1970 pp. 1-50).

Recently, it has been shown that neoplasia in ACR subjects was correlated with heightened susceptibility to transformation by KiMSV of skin fibroblasts (Pfeffer L. M., Kopelovich L.: "Differential Genetic Susceptibility of Cultured Human Skin Fibroblasts to Transformation by Kirsten Murine Sarcoma, Virus", *Cell.* 10:313-320, 1977). In this study, there also appeared to be a correlation heightened susceptibility to virus transformation of skin fibroblasts and loss of contact inhibition and decreased serum requirement for growth. However, an asymptomatic child of an ACR subject whose skin fibroblasts did not grow in decreased serum medium was highly susceptible to KiMSV transformation. The skin fibroblasts from ACR subjects were 100 to 1000-fold more susceptible to transformation by KiMSV than were normal cells (Kopelovich L.: "Phenotypic Markers in Human Skin Fibroblasts as Possible Diagnostic Indices of Hereditary Adenomatosis of the Colon and Rectum", *Cancer.* 40:2534-2541, 1977). The virus transformed skin fibroblasts formed tumors in athymic mice. These findings, as well as those described above, relative to heightened susceptibility of cultured skin fibroblasts to oncogenic virus transformation, point out the possible utility of this phenomenon for use as a diagnostic index not only for individuals with latent ACR, but those who are at high risk for other forms of cancer (Pfeffer L. M., Kopelovich L.: "Differential Genetic Susceptibility etc.", pp. 313-320; and Kopelovich L.: "Hereditary Adenomatosis of the Colon and Rectum-A Model of Tumor Progression", in S. Day (ed.) *1st International Workshop on Cancer Invasion and Metastasis: Biologic Mechanism and Therapy.* pp. 375-387, New York, Raven Press, 1977; and Kopelovich L., Pfeffer L., Lipkin M.: "Recent Studies on the Identification of Proliferative Abnormalities and of Oncogenic Potential of Cutaneous Cells in Individuals at Increased Risk of Colon Cancer", *Seminars in Oncology,* 3:369-372, 1976; and Pfeffer L., Lipkin M., Stutman O., Kopelovich L.: "Growth Abnormalities of Cultured Human Skin Fibroblasts Derived from Individuals with Hereditary Adenomatosis of the Colon and Rectum", *Journal of Cell Physiology,* 89-29-38, 1976; and Kopelovich, L., Conlon S., Pollack R.: "Defective Organization of Actin in Cultured Skin Fibroblasts from Patients with Inherited Adenocarcinoma", *Proceedings of the National Academy of Science, U.S.A.* 74:3019-3022, 1977), such as middled aged heavy smokers.

The present invention provides a method for determining the predisposition of a patient to the development of certain cancerous growths before such cancerous disorders have been estabished. Such growths are apparent in patients with lung cancer and occurs in certain familial disorders such as neurofibromatosis, an autosomal dominant disorder characterized by a very stron predisposition to malignancy.

The benefits derived from such a method are readily apparent even to the layman. If a patient is diagnosed according to the present invention to have a predispositon to cancer, several countermeasures can be used by the patient to reduce the possibility of developing cancer. Among these countermeasures, the more obvious one to be mentioned is the avoidance of the use by the patient of tobacco and excessive use of alcohol in conjunction with smoking. Additonally, if the patient so diagnosed lives in an area close to an airport, the possibility of developing cancer as a result of exposure to the combustion products of jet and rocket fuels is proportionately higher. By moving to a locally of decreased exposure, the possibility of developing cancer can be decreased thereby.

A patient who is diagnosed as having a predisposition to cancer may be working in an environment which is inducive to the occurrence of cancer. Environments of this nature are those in which the patient has close contact with asbestos.

The method of detecting a predisposition of a patient to cancer according to this invention, also provides a relatively simple, low cost tool which enables medical personnel to reliably determine whether a patient is at risk. If a patient is diagnosed as being at risk, preventative precautions can immediately be put into effect.

In addition to the advantages listed hereinbefore, the results obtained by the use of the technique of the present invention can be utilized as a basis for a gentic prenatal counseling tool. Up to the present, such counseling of prospective parents as to the possibility of their offspring having a higher than normal risk of developing cancer has proved extremely difficult. However, with the method of the present invention, a predisposition of the unborn child to certain cancers and/or certain other hereditary disorders could be determined and appropriate counsel given the parents to be.

The diagnostic technique of the present invention envisages a test kit for taking skin samples from patients and treating the same under laboratory conditions and includes an index for comparing the results obtained to such index to determine a predisposition to certain cancers and certain other hereditary disorders. Therefore, it is the primary object of this invention to provide a method of detecting a predisposition to certain cancers and certain other hereditary disorders which overcomes the aforementioned inadequacies of the prior art methods and provides an improvement which significantly contributes to the ease with which a predisposition to cancer can be detected.

Another object of the present invention is the provision of a method of testing a patient for the existence of certain cancers and certain other hereditary disorders.

A further object of the present invention is the provision of a method for testing a patient to determine a predisposition to certain cancers and certain other hereditary disorders which is relatively low in cost.

Another object of the invention is the provisionn of a method of testing the patient to determine a predisposition to certain cancers and certain other hereditary disorders wherein the method can be performed with the aid of a test kit.

Another object of the invention is to use the results of the test to provide a counseling tool relative to a wide variety of hereditary disorders such as certain prenatal hereditary disorders such as neurofibromatosis.

The foregoing has outlined some of the more pertinent objects of the present invention. These objects should be construed to be merely illustrative of some of the more prominent features and aplications of the invention. Many other beneficial results can be obtained by applying the disclosed invention in a different manner or modifying the invention within the scope of the disclosure, such as performing the diagnostic test in a matter of days, a DNA-probe prepared from Kirsten murine sarcoma virus in utilizing detection of expression of the cellular homology of the Kirsten murine sarcoma virus genome in patients' cells and/or amplification of the same gene (analogous to C. Ras). Particularly with regard to the use of the invention disclosed herein, this should not be construed as limited to a method of testing a patient to determine a predisposition to only lung cancer and neurofibromatosis, but should include a method for determining predisposition to certain other cancers, generally certain other hereditary diseases and the like.

SUMMARY OF THE INVENTION

The method of testing a patient to determine a predisposition to lung cancer and neurofibromatosis according to the present invention is defined by the appended claims with a specific embodiment shown in the attached drawing. For the purpose of summarizing the invention, the invention relates to a method of testing a patient to determine a predisposition to lung cancer, neurofibromatosis, and the like. The method includes the steps of carrying out a biopsy on each patient of a first group of patients who are known to have lung cancer, clinical neurofibromatosis or in families with the disorder. The biopsy includes the removal of a skin sample from each patient. The skin samples are prepared in readiness for in vitro testing thereof. An in vitro test is performed relative to each skin sample to ensure absence of bacterial or mycoplasma contamination. Various portions of Kirsten murine sarcoma virus are prepared and each cell culture prepared from proven uncontaminated skin samples is treated with a portion of the Kirsten murine sarcoma virus. The treated skin cultures are incubated and an assay carried out to determine which skin cultures have been transformed or changed due to treatment with Kirsten murine sarcoma virus. The various steps carried out relative to the skin cultures for the first group of patients with lung cancer or neurofibromatosis are then performed on the skin cultures taken from a second group of control patients who are aged-matched to the first group and who are known to be cancer and neurofibromatosis free and free of all other familial disorders. From the results of the assays carried out relative to the first and to the control second groups of patients, an index is composed. The index is used to determine the predisposition of a subsequent patient to lung cancer or neurofibromatosis. This determination is accomplished by a comparison of the results obtained by carrying out the various steps relative to the first group of patients on the subsequent patient against the results that have already been indexed.

More specifically, with regard to the treatment of skin samples with portions of Kirsten murine sarcoma virus, each portion of Kirsten murine sarcoma virus is prepared serially in various degrees of dilution. Replicate cell cultures prepared from skin samples taken from pateints with lung cancer or neurofibromatosis are treated with a portion of Kirsten murine sarcoma virus of a particular dilution. From the assay, results are obtained as to the Kirsten murine sarcoma virus of greatest dilution that has the effect of transformation or causing microscopic changes in the cell cultures prepared from a particular skin sample.

The foregoing has outlined rather broadly the more pertinent and important features of the present invention in order that the detailed description of the invention that follows may be better understood so that the present contribution to the art can be more fully appreciated. Additionally, features of the invention will be described hereinafter which form the subject of the claims of the invention. It should be appreciated by those skilled in the art that the conception and specific embodiment disclosed may be readily utilized as a basis for modifying or designing other devices for carrying out the same purposes as the present invention. It should be realized by those skilled in the art that such equivalent methods do not depart from the spirit and scope of the invention as set forth in the appended claims.

BRIEF DESCRIPTION OF THE DRAWINGS

For a fuller understanding of the nature and objects of the invention, reference should be had to the following description taken in conjunction with the accompanying drawing in which:

The drawing is a schematic, block diagram showing the various steps included in the present invention.

DETAILED DESCRIPTION

Figure 1:
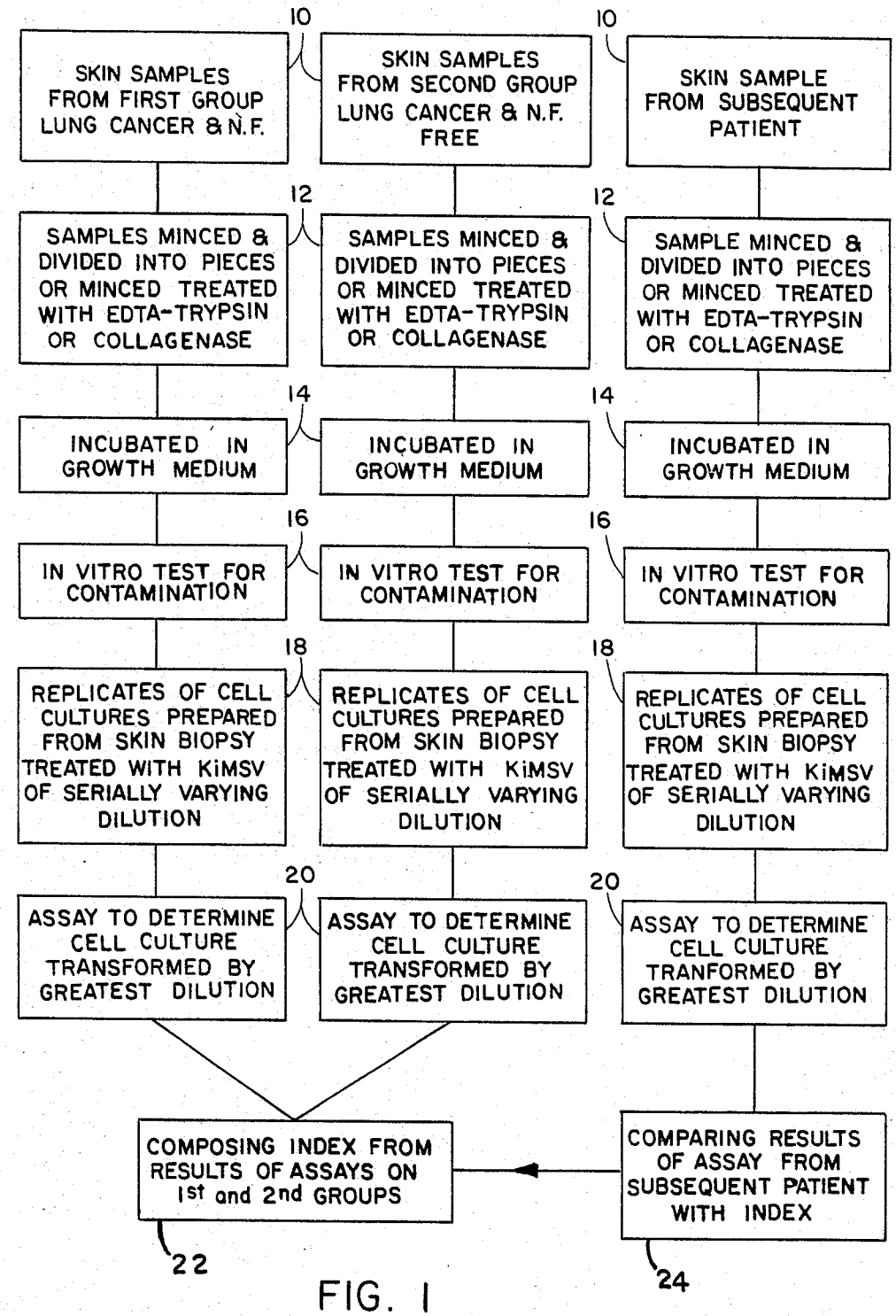

FIG. 1 is a schematic block diagram showing the various steps included in the method of testing a patient for determining a predisposition to cancer, as exemplified by lung cancer, and hereditary diseases such as neurofibromatosis and the like. In this method, 10 represents the step of taking a skin sample from each of a plurality of patients from a first group of patients known to have lung cancer or neurofibromatosis. In practice, a skin sample approximately 2-4 mm in diameter is obtained by carrying out a biopsy on each patient. The biopsy is performed by means of a punch biopsy taking the skin sample from a cosmetically unimportant area of the patients's body. This skin sample is usually taken from the area of the trapezius muscle in the region between the patient's neck and shoulder extremity. A skin sample taken from a patient is collected aseptically in a sample container and labelled. The sample container into which the skin sample is deposited contains cold Leibovitz L-15 medium which provides a stable pH during transport of the skin sample tissue from the surgery to a cell culture laboratory. More specifically, the Leibovitz collection medium L-15 includes 2% heated fuel bovine serum, hereinafter to as FBS, 100 micrograms per milliliter of the antibiotic gentomycin and 50 micrograms per milliliter of fungizone. Fungizone is a registered trade mark. This self buffering growth medium provides a stable degree of acidity during transportation of the sample.

At the cell culture laboratory, as represented by the step 12 of the drawing, each of the skin samples from the first group of patients is transferred into a cell culture dish. The collection medium is withdrawn and the sample is minced with the aid of a sharp surgical scalpel to provide a plurality of small pieces of tissue. The small pieces of tissue are placed within two plastic petri dishes such that between four and five pieces of tissue are placed in each petri dish. The dishes conveniently are of the type having an external diameter of 60 mm. The pieces of tissue within both of the covered petri dishes are incubated for one hour at approximately 37° C.

The third step involved in the diagnostic technique is generally designated by the block 14 shown in the drawing. Included in this third step is the addition to each of the pieces of tissue within a petri dish of a growth medium. Such a growth medium comprises a minimum essential medium in an Earle's balanced salt solution. For a 3 milliliter volume of growth medium hereinafter referred to as GM, the salt solution is supplemented with 2 millimoles of glutamine and 20% by volume FBS and 100 Units of penicillin, 100 micrograms of streptomycin and 25 micrograms of fungizone. The growth medium is carefully added to the pieces of tissue within the petri dishes so that the pieces of tissue adhering to the plastic dishes are not dislodged there-from. The two petri culture dishes containing the pieces of tissue from a skin sample are placed in an incubator. The incubator is maintained at a thermostatically controlled temperature and has a controllable atmosphere. The temperature is maintained at 37° C. for a period of seven to twenty-one days and the atmosphere comprises air with an addition of 5% by volume of carbon dioxide. The culture medium within the dishes is changed approximately every three days. Within seven to twenty-one days of incubation depending upon the time required for the development of monolayers on the pieces of tisue, the cells of the monolayers are removed. The cells of the monolayers are removed by means of EDTA-trypsin mixture. The monolayer cells are pooled from the two petri dishes and are washed. The pooled and washed cells are then transferred to two 120 mm culture dishes containing 5 milliliters of GM and are incubated at 37° C. under the same conditions as described hereinbefore.

Alternatively, the original minced tissue is treated at 4° C. in conjunction with EDTA-trypsin as collagenase and monolayers directly prepared as described immediately below.

At this stage, the fourth step, as represented by the numeral 16 shown in the drawing is carried out. The fourther step involves removal of a quantity of the monolayer cells and testing the cells for the presence of contaminating bacteria or mycoplasma. The monolayer cells removed for monitoring if established as free from contamination, are then stored in liquid nitrogn as a useful resource of such cells for future use.

Having confirmed the absence of contamination relative to the monolayer cells, a plurality of portions of Kirsten murine sarcoma virus are prepared. The preparation of the Kirsten murine sarcoma virus portions is included in the fifth step generally designated by the numeral 18 of the drawing.

The Kirsten murine sarcoma virus is prepared in a normal rat kidney cell line referred to hereinafter as a NRK cell line transformed in vitrol by the Kirsten murine sarcoma virus. The resultant fluids are harvested 48 hours after the transformation or change. The resultant fluid is clarified by centrifugation and then passed through a 45 micron Millipore filter and stored in liquid nitrogen until required. The Kirsten murine sarcoma virus preparation is special in that it has been purified over a three-year period by obtaining a very special clone that produces rapid and repetitive transformation. This cloned Kirsten murine sarcoma virus, which has also been passed through human skin fibroblast cells to be used in the viral transformation tests, is an important feature in this work and can be used to prepare the DNA probe to be utilized in the detection of expression of the cellular homolog of the Kirsten murine sarcoma virus genome in patient's cells and/or amplification of the same gene (analagous to C. Ras).

Each of the portions of Kirsten murine sarcoma virus required to treat a plurality of portions of monolayer cells are serially diluted by a factor of 10 such that the Kirsten murine sarcoma virus diluted in the ration 1:10$^1$, 1:10$^2$, 1:10$^3$, etc., to 1:10$^n$ where n represents the number of portions of Kirsten murine sarcoma virus. In practice, it has been found that the provision of three portions of Kirsten murine sarcoma virus is adequate having respective dilutions of 1:10, 1:100 and 1:1000, respectively.

The monolayer cells are removed from the two 120 mm petri dishes and are divided into portions of approximately 10$^5$ cells each. The monolayer cell portions are then divided into two groups. One portion of cells from each group is inoculated with a Kirsten murine sarcoma virus portion of 1:10 dilution. Another portion of cells from each group is inoculated with a Kirsten murine sarcoma virus portion of 1:100 dilution. Finally, a third portion of cells from each group is inoculated with the Kirsten murine sarcoma virus portion having a dilution ratio of 1:1000.

An assay is carried out to determine the greatest dilution of Kirsten murine sarcoma virus that is capable transforming the monolayer cells.

The viral assay commences one day after the cells have been inoculated with Kirsten murine sarcoma virus. During this twenty-four hour period, the cultures are treated for one hour at 37° C. with DEAE-dextran having a molecular weight greater than 2X10$^6$ daltons. The final concentration of the dextran being 25 micrograms per milliliter in a total incubation volume of 4 milliliters. The quantity of Kirsten murine sarcoma virus inoculated into this liquid is 0.25 milliliters. In each case the Kirsten murine sarcoma virus portions are serial 10-fold dilutions such as 10$^{-1}$ to 10$^{-3}$ of the standard frozen Kirsten murine sarcoma virus stock.

A portion of monolayer culture cells from each group is inoculated with a portion of Kirsten murine sarcoma virus of a particular dilution and the dextran growth solution replenished as necessary. The cultures are maintained at 37° C. and the culture cells observed after fourteen days to ascertain the greatest dilution of Kirsten murine sarcoma virus capable of transforming the culture cells. Transformation of the culture cells is characterized by a cytological change relative to one or more surface areas of the culture cells. Two almost identical groups of cell cultures are used in order to duplicate the tests. This duplication of tests has the effect of increasing the accuracy of the test results. In each test peformed relative to a duplicate pair of cell culture portions, the greatest dilution of Kirsten murine sarcoma virus required to transform at least one of the duplicated portions is taken as the assay result.

The assay to determine the portion of cell cultures transformed by the greatest dilution of Kirsten murine sarcoma virus is designated by the numeral 20 of the drawing. The criteria for categorizing a particular portion of cell cultures as being transformed by the portion of Kirsten murine sarcoma virus is whether the dilution of Kirsten murine sarcoma virus was equal to or above 1:10$^1$. The morphological alterations or change in structure or form of the culture cells due to the treatment with Kirsten murine sarcoma virus is characterized by refractile spindle-shaped and round cells which grow on top of the monolayers and exhibit large cytoplasmic vacuoles.

In order to control the quality and strength of the Kirsten murine sarcoma virus used in the assay, the titer or standard strength per volume of the Kirsten murine sarcoma virus stock solution is assayed for conformity in NRK cells. The greatest dilution of Kirsten murine sarcoma virus required to transform a given portion of culture cells is recorded as the transformation dilution endpoint, referred to hereinafter as an "endpoint".

A skin sample is taken from a plurality of patients within a first group known to have cancer, a cancer-related disease or a hereditary disorder. The various steps 10-20 are described hereinbefore are carried out relative to these skin samples. The steps 10-20 are repeated using skin samples taken from a plurality of patients within a second group known to be cancer-free, in families without either a cancer history or any disorder with a hereditary component. Using the endpoint results of the assay relative to the skin samples of the first and second group of patients, an index is composed which is designated 22 on the accompanying drawing.

In order to ascertain whether a subsequent patient has a predisposition to neurofibromatosis, the various steps 10-20 described hereinbefore are performed relative to a skin sample taken from the subsequent patient. The result of the assay on the skin sample of the subsequent patient is compared with the index 22. The comparison of the assay results relative to the subsequent patient is designated 24 in the accompanying drawing.

Actual experiments were carried out according to the sequence of steps outlined hereinbefore to establish a comparison of culture cells transformed by Kirsten murine sarcoma virus. Cultured cells, otherwise called skin fibroblasts, hereinafter referred to as SF, were established from a first group of patients known to have lung cancer or neurofibromatosis. SF were established from a control second group of normal, age-matched control patients. A comparison of the assay results relative to the first and second groups respectively revealed a significant majority of the SF relative to the first group of patients were transformed as compared to the SF relative to the control second group.

For the lung cancer group, a total of 13 viral transformation diagnostic tests were performed with SF cultures from 73 cancer patients with pathologically certified lung cancer and 94 controls of the second group without any cancer. The results are shown in the table, designated TABLE I and shown that 69 percent of the cultured SF from lung cancer patients were transformed and only 4 percent of the cultured SF from the second control group were transformed.

TABLE I

| Type | Group Total # Tested | Number Positive Transforms |
|---|---|---|
| 1st Group | | |
| lung cancer | 73 | 52 (71%) |
| 2nd Group | | |
| controls normals | 94 | 4 (4%) |

Mean age of the first group with lung cancer is 60.6 years, and for the second normal control group, 58.8 years.

Three years after the information in TABLE I was obtained, SF frozen in liquid nitrogen were re-tested in the viral transformation test. The designation of SF from each patient in the first group with lung cancer and the second normal control group were re-coded by an outside person to test whether the same results could be obtained three years later. There is 100% agreement between the original tests with a total of 36 re-coded SF from lung cancer patients in the first group and 29 SF from normal control patients in the second group. The second round of tests shows the standardization, conformity and reproducibility of the test.

Other tests have now been done with SF cultures established from patients with another cancer, skin cancer, and in each case the cultures were positive by the viral transformation assay with other cancers, such as skin cancer (3 of 4 positive), liver cancer (1 of 4 positive) and leukemia (2 of 2 positive), and in each case, the skin fibroblast cultures were positive by the viral transformation assay. Skin fibroblast cultures from patients with emphysema were also positive (2 of 3 positive) in the viral transformation test. This shows the probable general utility of the test to predict those persons that might be determined to develop cancer.

In studies with neurofibromatosis, transformation of the SF relative to a first group with neurofibromatosis was observed regardless of whether individual patients within the first group came from families with a history of neurofibromatosis or not. The following table, designted TABLE II, provides details of the patients within the first group of patients and includes those patients having clinically diagnosed neurofibromatosis or those patients not having symptoms of neurofibromatosis but coming from families having a history of neurofibromatosis.

TABLE II

| Code | NF | Age | Sex | Cafe-au-lait | Neuromas | Aux. Freckles |
|---|---|---|---|---|---|---|
| A | Yes | 40 | F | Yes | Yes | Yes |
| B | Yes | 24 | F | Yes | Yes | Yes |
| C | Yes | 71 | M | Yes | Yes | Yes |
| D | Yes | 1½ | M | Yes | Yes | Yes |
| E | Yes | 30 | F | Yes | Yes | Yes |
| F | Yes | 30 | F | Yes | Yes | Yes |
| G | Yes | 55 | F | Yes | Yes | Yes |
| H | Yes | 12 | F | Yes | Yes | Yes |
| I | No | 33 | F | No | No | No |
| J | No | 24 | F | No | No | No |
| K | No | 25 | M | No | No | No |
| L | No | 42 | F | No | No | No |

Referring to Table II, the patient with Code B suffered from a skeletal abnormality. Patient D had hemangioma or a benign tumor of dilated blood vessel. Patient F suffered from adenocarcinoma of the lung. Patient I had cystic hydroma.

Cafe-au-lait spots are spots of patch pigmentation of the skin, usually light brown in color, that are characteristic of neurofibromatosis, but may also be found in some normal individuals.

TABLE III shows the Kirsten murine sarcoma virus endpoints for SF cultures established from patients within the first group of patients. Persons listed in category 1 had all been clinically diagnosed as having neurofibromatosis. The first group is divided into two categories, category 1 showing those with symptoms of neurofibromatosis and category 2 showing those without symptoms of neurofibromatosis but having a family history of neurofibromatosis. Table III also indicates positively or negatively as to whether the particular patient came from a family having a history of cancer. Category 3 shows those age-matched, normal patients without neurofibromatosis or a family history of the same.

TABLE III

| GROUP I | | | | | | GROUP II | | |
|---|---|---|---|---|---|---|---|---|
| Category 1 Symptomatic Patients | | | Category 2 Asymptomatic Patients | | | Category 3 Asymptomatic Patients | | |
| Code | Family History of Cancer | Assay Results | Code | Family History of cancer | Assay Results | Code | Family History of cancer | Assay Results |
| A | Yes | 1 | I | Yes | 2 | M | No | 1 |
| B | Yes | 2 | J | Yes | 1 | N | No | 1 |
| C | Yes | 1 | K | Yes | 2 | O | No | 1 |
| D | Yes | 1 | L | Yes | 3 | P | No | 1 |
| E | Yes | 1 | Total 4 patients | | | Q | No | 1 |
| F | Yes | 2 | | | | R | No | 1 |
| G | Yes | 2 | | | | S | No | 1 |
| H | No | 1 | | | | T | No | 1 |
| Total 8 patients | | | | | | U | No | 1 |
| | | | | | | V | No | 1 |
| | | | | | | W | No | 1 |
| | | | | | | X | No | 1 |
| | | | | | | Y | No | 1 |
| | | | | | | Z | No | 1 |
| | | | | | | Total 14 patients | | |

From the results obtained by reference to Table III, it is observed that positive transformations by Kirsten murine sarcoma virus occurred relative to patients A, B, E, F and G and negative transformations occurred relative to patients C, D, and H. The criterion for establishing whether a patient is categorized as a positive or negative transformation depends upon whether the greatest dilution of Kirsten murine sarcoma virus transforming dilution is equal to or greater than 1. If this is the case, the transformation is positive. In the case of patients C, D and H, all the dilutions are less than 1 and so the transformations are classified as negative.

Therefore, for the first category of Table III, which relates to those patients known to have cancer, the ratio of positive transformations to total number of patients within the first category is 5.8 or 63%.

Category 2 of Table III is a list of the patients included in Table II who exhibit no clinical symptoms of neurofibromatosis but who come from a family having a history of cancer. Of these patients, patients I, K and L are positive as defined hereinbefore whereas patient J is negative. From these results it is observed that the ratio of positive transformations relative to the total number of patients within Category 2 is 3:4 or 75%.

Category 3 of Table III is a list of normal, age-matched patient controls having no clinically diagnosed cancer and no family history of cancer. Of these patients, patient M was positive as defined hereinbefore, whereas patients N-Z were negative. From these results it is observed that the ratio of positive transformations relative to the total number of patients within Category 3 is 1:14 or 7%.

From the results obtained from Table III it is readily apparent that patients with the highest disposition to cancer are those of Category 2 and those with the lowest disposition to cancer are those of Category 3.

The mean age in years for patients within Categories 1-3 were 33, 31 and 29 years respectively.

By means of a comparison of the results for Categories 1, 2 and 3 of Table III, an index is established. The index is used as an aid in determining the predisposition to cancer of a subsequent patient. The subsequent patient is subjected to a biopsy and the various steps described hereinbefore are performed relative to the skin sample of the subsequent patient. The results of the assay relative to the subsequent patient are compared with the index to determine whether the subsequent patient has a predisposition to cancer.

Therefore, the in vitro virus transformation assay of the present invention provides an excellent diagnostic tool for identifying individuals genetically a risk for neurofibromatosis. Although the presence of Cafe-au-lait spots, freckles and neurofibromas have been considered indicative of a predisposition to neurofibromatosis, such features are by no means reliable indicators thereof. The present invention provides a reliable index for determining a predisposition to neurofibromatosis and thereby affords the opportunity of the patient so diagnosed to take the necessary steps to avoid the development of this disorder. Since the control group of normal patients in Table I showed 4% of patients positive in the test and 7% of Category 3 normals in Table III are positive in the test, these could represent those persons in the population who are destined to destroy cancer and hereditary disease later on in life. Amniotic fluid was obtained from a single patient with neurofibromatosis and the cells obtained and cultured. The Kirsten murine sarcoma virus test was performed on the cells and was positive. In this way, it may be possible to perform a prenatal examination to predict possible hereditary disorders that could lead to problems in the fetus and later on such as neurofibromatosis, other cancers and a variety of other familial problems. In another very recent study with von Recklinghausen's neurofibromatosis only, (and eliminating central or bilateral acoustic neurofibromatosis), 6 of 8 with the disease were positive in the viral transformation test compared with only 1/11 non-affected relatives.

The present invention includes that contained in the appended claims as well as the foregoing description. Although this invention has been described in its preferred form with a certain degree of particularity, it is understood that the present disclosure of the preferred form has been made only by way of example and that numerous changes in the details relative to the performance of the respective steps may be resorted to without departing from the spirit and scope of the inventon. Many other beneficial results can be obtained by applying the disclosed invention in a different manner or modifying the invention within the scope of the disclosure, such as performing the diagnostic test in a matter of days, a DNA-probe prepared from Kirsten murine sarcoma virus is utilized to detct expression of the cellular homolog of the Kirsten murine sarcoma virus genome in patients' cells and/or amplification of the same gene (analogous to C. Ras). Particularly with regard to the use of the invention disclosed herein, this should not be construed as limited to a method of testing a patient to determine a predisposition to only lung cancer and neurofibromatosis, but should include a method for determining predisposition to certain other cancers, generally certain other hereditary diseases and the like.

What is claimed is:

1. A method of diagnostically testing a patient for degree of risk for the particular presence of lung cancer, skin cancer, liver cancer, leukemia, neurofibromatosis or emphysema which comprises the steps of:

carrying out a biopsy on each patient of a first group of patients known to have lung cancer, skin cancer, liver cancer, neurofibromatosis or emphysema, the biopsy including the removal of a skin sample from each of the patients of the first group;

preparing the skin samples removed from the first group of the patients for in vitro testing thereof;

performing in vitro testing of the skin samples of the first group of patients to determine the existence of bacterial and mycoplasma contamination;

preparing portions of Kirsten murine sarcoma virus;

treating the uncontaminated prepared skin cells of the first group of patients with the prepared portions of Kirsten murine sarcoma virus;

incubating the virus treated skin cells of the first group of patients;

carrying out a viral assay upon the incubated treated skin cells to determine which skin samples have been transformed due to the treatment with Kirsten murine sarcoma virus and to determine the greatest dilution of Kirsten murine sarcoma virus that is capable of transforming the cells characterized by a cytological change relative to one or more surface areas of the culture cells;

repeating the foregoing steps carried out relative to the skin cell cultures taken from the first group of patients of skin cells obtained by carrying out a biopsy on each patient of a second group of cancer and hereditary disease-free patients;

composing an index from a comparison of the results obtained from the assay relative to the first group of patients with the results obtained from the assay relative to the second group of patients;

repeating the foregoing steps relative to the first group of patients on a test patient utilizing either a skin sample or an amniotic fluid sample to obtain cells for in vitro testing where the predisposition of the subsequent patient to lung cancer, skin cancer, liver cancer, leukemia, neurofibromatosis or emphysema is not known; and utilizing the index to determine whether a predisposition to lung cancer, skin cancer, liver cancer, leukemia or emphysema exists relative to the test patient by a comparison of the results obtaned by the assay to determine the greatest dilution of Kirsten murine sarcoma virus that is capable of transforming the cells characterized by a cytological change relative to one or more surface areas of the culture cells carried out relative to the test patient with the index.

2. The method as set forth in claim 1 wherein skin cells are removed from the patient by punch biopsy.

3. The method as set forth in claim 1 wherein the skin sample is removed from the patient and aseptically transferred to a self-buffering medium to provide a stable pH value for the skin sample.

4. The method as set forth in claim 3 wherein the self-buffering medium is cold relative to the ambient temperature.

5. The method as set forth in claim 4 wherein the self-buffering medium is Leibovitz L-15 medium including fetal bovine serum, gentomycin and fungizone.

6. The method as set forth in claim 5 wherein the Leibovitz medium includes fetal bovine serum within the rage 1-10%, gentamycin within the range 50-200 micrograms per milliliter, and fungizone within the range 10-100 micrograms per milliliter.

7. The method as set forth in claim 6 wherein the fetal bovine serum is heated.

8. The method as set forth in claim 3 wherein the skin sample is finely minced or treated overnight at 4° C. directly with EDTA-trypsin or collagenase.

9. The method as set forth in claim 8 wherein a growth medium is added to a portion of the minced skin sample or to the portion treated with EDTA-trypsin or collagenase.

10. The method as set forth in claim 9 wherein the growth medium comprises minimal essential medium, Earle's balanced salt solution, the salt solution being supplemented by glutamine, fetal bovine serum, penicillin, streptomycin and fungizone.

11. The method as set forth in claim 10 wherein the growth medium has a volume of 3 milliliters, the glutamine is within the range 1-5 mM, the fetal bovine serum is within the range 5-50% by volume, the penicillin is within the range 50-150 units, the streptomycin is within the range 50-150 micrograms and the fungizone is within the range 5-50 micrograms.

12. The method as set forth in claim 10 wherein for a growth medium having a volume of 3 milliliters, the glutamine is 2 mM, the fetal bovine serum is 20% by volume, the penicillin is 100 units, the streptomycin is 100 micrograms and the Fungizone is 25 micrograms.

13. The method as set forth in claim 10 wherein for a unit volume of salt solution in milliliters, the glutamine is 0.66 mM, the fetal bovine srum is 20% by volume, the penicillin is 33 units, the streptomycin is 33 micrograms and the Fungizone is 8.33 micrograms.

14. The method as set forth in claim 8 wherein the skin sample is subjected to incubation.

15. The method as set forth in claim 14 wherein the skin sample is subjected to a temperature within the range 30°-40° C. for a period of between one-half to two hours.

16. The method as set forth in claim 15 wherein the skin sample is subjected to a temperaure of approximately 37° C. for a period of approximately one hour, or overnight at 4° C. with EDTA-trypsin or collagenase.

17. The method as set forth in claim 9 wherein the skin sample or the EDTA-trypsin or collagenase-treated cells with the growth medium are subjected to incubation.

18. The method as set forth in claim 17 wherein the skin sample or the EDTA-trypsin or collagenase-treated skin samples within the growth medium are subjected to a temperature of 37° C. for a period of one to twenty-eight days within an atmosphere comprising air to which is added an additional 5% by volume of carbon dioxide.

19. The method as set forth in claim 17 wherein the monolayer of incubated cells of the skin sample are removed by means of a EDTA-trypsin mixture, the removed cells are washed and transferred to a growth medium.

20. The method as set forth in claim 19 wherein the cells are subjected to a temperature of approximately 37° C. for a further perid within the range of seven to twenty-one days, within an atmosphere comprising air to which is added an additional 5% by volume of carbon dioxide, the atmosphere being changed approximately every three days.

21. The method as set forth in claim 20 wherein a portion of the prepared skin cells are monitored to establish the absence of bacterial contamination and mycoplasma and the monitored sample is stored in liquid nitrogen.

22. The method as set forth in claim 21 wherein the Kirsten murine sarcoma virus is produced by the rat kidney cell line in vitro and the Kirsten murine sarcoma virus is purified and a special clone prepared by passage through human skin fibroblasts.

23. The method as set forth in claim 1 wherein the uncontaminated prepared cultured skin cells from the patient are inoculated into a plurality of containers; a portion of DEAE-dextran is added to each container, and the resultant culture mixture is incubated for approximately one hour at approximately 37° C.

24. The method as set forth in clam 23 wherein a portion of standard frozen Kirsten murine sarcoma virus stock is added to the culture mixture within each container.

25. The method as set forth in claim 23 wherein the dextran has a molecular weight greater than $2 \times 10^6$ daltons and a concentration of approximately 25 micrograms per milliliter where the total incubation volume within each container is approximately 4 milliliters.

26. The method as set forth in claim 24 wherein each portion of the Kirsten murine sarcoma virus is approximately 0.25 milliliters by volume.

27. The method as set forth in claim 1 wherein the viral assay includes observing the highest dilution of Kirsten murine sarcoma virus that induces transformation of the uncontaminated prepared cultured skin cells after removing from the patient within a unit period of time.

28. The method as set forth in claim 27 wherein the induced transformation includes a cytological change in at least one area.

29. The method as set forth in claim 28 wherein the unit period of time is approximately 14 days.

30. The method as set forth in claim 1 wherein analyzing of the results of the viral assay includes comparing the transformation results relative to skin samples taken from patients known to have lung cancer or neurofibromatosis with the transformation results relative to skin samples taken from normal patients which have been age matched to the patients known to have lung cancer or neurofibromatosis.

31. The method of claim 1 for diagnostically testing a patient for a degree of risk for the presence of lung cancer.

32. The method of claim 1 for diagnostically testing a patient for a degree of risk for the presence of neurofibromatosis.

* * * * *

UNITED STATES PATENT AND TRADEMARK OFFICE
CERTIFICATE OF CORRECTION

PATENT NO. : 4,582,787
DATED : April 15, 1986
INVENTOR(S) : Frankel

It is certified that error appears in the above-identified patent and that said Letters Patent are hereby corrected as shown below:

At column 8, line 39, delete "fungizone" and insert --Fungizone--.

At claim 5, line 3, delete "fungizone" and insert --Fungizone--.
At claim 6, line 3, delete "fungizone" and insert --Fungizone--.
At claim 10, line 4, delete "fungizone" and insert --Fungizone--.
At claim 11, line 5, delete "fungizone" and insert --Fungizone--.

Signed and Sealed this

Fifth Day of August 1986

[SEAL]

Attest:

Attesting Officer

DONALD J. QUIGG

Commissioner of Patents and Trademarks